United States Patent
Bonomi (10) Patent No.: US 11,076,767 B2
(45) Date of Patent: Aug. 3, 2021

(54) METHOD AND SYSTEM OF MONITORING CARDIAC ACTIVITY OF A USER

(71) Applicant: KONINKLIJKE PHILIPS N.V., Eindhoven (NL)

(72) Inventor: Alberto Giovanni Bonomi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 154 days.

(21) Appl. No.: 16/464,404

(22) PCT Filed: Nov. 23, 2017

(86) PCT No.: PCT/EP2017/080137
§ 371 (c)(1),
(2) Date: May 28, 2019

(87) PCT Pub. No.: WO2018/099790
PCT Pub. Date: Jun. 7, 2018

(65) Prior Publication Data
US 2020/0337572 A1 Oct. 29, 2020

(30) Foreign Application Priority Data
Nov. 29, 2016 (EP) ..................... 16201124

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0006* (2013.01); *A61B 5/1102* (2013.01);
(Continued)

(58) Field of Classification Search
None
See application file for complete search history.

(56) References Cited

U.S. PATENT DOCUMENTS

| 6,701,183 B2 | 3/2004 | Baker et al. |
| 9,179,849 B1 | 11/2015 | Brady et al. |
| (Continued) | | |

FOREIGN PATENT DOCUMENTS

| WO | 2015150199 A1 | 10/2015 |
| WO | 2016003269 A1 | 1/2016 |

OTHER PUBLICATIONS

International Search Report and Written Opinion, International Application No. PCT/EP2017/080137, dated Feb. 1, 2018.
(Continued)

*Primary Examiner* — Brian T Gedeon (57) ABSTRACT

A method of monitoring cardiac activity of a user is provided. Heart beat time data is detected by a PPG sensor (110) in a health sensor (100) worn by the user (1). Motion data is detected by a motion sensor (120) in the health sensor (100). The output data of the PPG sensor (110), which comprises heart beat time data, is analyzed to detect arrhythmia periods. The detected heart beat time data, the detected motion data and the detected arrhythmia are forwarded to an external device, where the data can be stored. The output data of the PPG sensor (110) comprising the heart beat time data, the detected motion data and the detected arrhythmia periods are displayed such that a medical professional (2) can analyze this data to determine whether a suspected arrhythmia period is valid.

8 Claims, 5 Drawing Sheets

(51) Int. Cl.
*G16H 80/00* (2018.01)
*A61B 5/11* (2006.01)
*A61B 5/361* (2021.01)
*A61B 5/363* (2021.01)

(52) U.S. Cl.
CPC .............. *A61B 5/361* (2021.01); *A61B 5/363* (2021.01); *A61B 5/681* (2013.01); *A61B 5/721* (2013.01); *A61B 5/7282* (2013.01); *A61B 5/74* (2013.01)

(56) References Cited

U.S. PATENT DOCUMENTS

| | | | |
|---|---|---|---|
| 10,398,381 B1 * | 9/2019 | Heneghan | ............ A61B 5/7282 |
| 2015/0065891 A1 | 3/2015 | Wiesel | |
| 2015/0223705 A1 | 8/2015 | Sadhu | |

OTHER PUBLICATIONS

Heuvel, L., "The occurrence of arrhythmias during daily living", Personal Health department, Philips Research, Eindhoven, The Netherlands, Jul. 2016.

\* cited by examiner

METHOD AND SYSTEM OF MONITORING CARDIAC ACTIVITY OF A USER

This application is the U.S. National Phase application under 35 U.S.C. § 371 of International Application No. PCT/EP2017/080137, filed on 23 Nov. 2017, which claims the benefit of European Application Serial No. 16201124.1, filed 29 Nov. 2016. These applications are hereby incorporated by reference herein.

FIELD OF THE INVENTION

The invention relates to a method and system of monitoring cardiac activity of a user.

BACKGROUND OF THE INVENTION

One cardiac condition which needs to be monitored is atrial fibrillation AF. Atrial fibrillation AF can lead to embolic stroke and heart failure. Therefore, an early detection of atrial fibrillation AF is required. However, the detection of AF can be problematic as AF can appear suddenly and stop autonomously. Hence, long term monitoring of the cardiac activity of a user is required if AF events are to be captured effectively. A long term monitoring of the cardiac activity of the user is however often obtrusive and costly as the required devices such as a Holter monitor is expensive. While the Holter monitor can efficiently collect the patient's ECG, such a Holter monitor is obtrusive such that a long term monitoring can be quite cumbersome for a user.

Wearable devices which comprise a photo-plethysmographic PPG sensor are known which are able to unobtrusively detect a heart rate and heart rhythm of a user. WO 2005/150199 discloses a system for detecting variations of a heart rate of a user. A PPG sensor is used to measure a heart beat-related optical signal. Heart beat variations are derived from the heart beat-related optical signal. In an analyzing unit, the derived heart rate variation signal is compared to a reference heart rate range.

U.S. Pat. No. 9,179,849 discloses a method of monitoring cardiac activity of a user. A heart rate and motion data is detected and analyzed.

SUMMARY OF THE INVENTION

It is an object of the invention to provide a method of monitoring cardiac activity of a user in an unobtrusive manner to efficiently detect atrial fibrillation.

According to the invention, a method of monitoring cardiac activity of a user is provided. Heart beat time data is detected by a photo-plethysmographic PPG sensor in a health sensor, such as a wearable health sensor worn by the user. Motion data is detected by a motion sensor in the health sensor. The output data of the PPG sensor, which comprises heart beat time data, is analyzed to detect suspected arrhythmia periods. The detected heart beat time data, the detected motion data and the detected arrhythmia periods are forwarded to an external device, where the data can be stored. The output data of the PPG sensor comprising the heart beat time data, the detected motion data and the raw signal or data as detected during the detected arrhythmia periods are displayed such that a medical professional can analyze this data to determine whether a suspected arrhythmia period is valid.

A message is output to the user to operate a specific movement protocol with the body part where the health sensor is located to avoid motion artefacts in the output signal of the PPG sensor when the suspected arrhythmia period is detected.

A health sensor position and orientation is detected based on the detected motion data. Data templates of heart rate time data and heart rate time signal waveforms are generated during the detection of the heart beat time data. A data template is selected to compare with the current measurement according to position and orientation of the sensor. The selected data template is displayed together with the output signal of the PPG sensor.

According to an aspect of the invention, user symptoms are inputted by the user, heart rate rhythm irregularities in the output data of the PPG sensor are detected and the user symptoms and the heart rate rhythm irregularities are displayed together with the output signal of the PPG sensor.

According to an aspect of the invention, the arrhythmia period is an atrial fibrillation period, a heart beat pause period, a tachycardia period, a bradycardia period or supraventricular arrhythmia periods.

According to an aspect of the invention, a system and method for monitoring cardiac activity of a user is provided. A health sensor, such as for example a wearable health sensor, which comprises a photo-plethysmographic PPG sensor as well as a motion sensor or an acceleration sensor, which may be worn on the skin of the user in order to detect heart rate data and the motion of the user. The PPG sensor provides a signal which changes its amplitude with the occurrence of heart beats which cause pulsatile volumetric variation in the blood underneath the skin surface. Thus, the PPG sensor detects heart rate data and the output signal of the PPG sensor comprises heart rate data. The heart rate data can be heart beat time data and/or heart beat rhythm data. As the sensor may be a wearable sensor like a wrist worn sensor or a sensor worn in or behind the ear of a user, the detection of heart rate data can be performed unobtrusively. The sensor can detect the heart rate or cardiac activity of a user as well as its motion. The PPG signal used to derive heart rate (like heart beat time data) and the heart rhythm information can be analyzed in order to detect an atrial fibrillation AF. The analysis can be performed in the sensor or externally from the sensor. The heart rate data (like heart beat time data), the motion data and optionally the analysis of the heart rate data (like heart beat time data) can be forwarded to an external device (which can be a backend unit or a cloud unit) via wires or wirelessly. The data can be stored in the backend unit or the cloud unit.

The data can be further processed and analyzed in order to detect an atrial fibrillation AF. If an atrial fibrillation AF is detected or analyzed, then the corresponding PPG data which includes heart rate data and motion data can be displayed such that a clinical professional can analyze such data in order to determine whether the detected atrial fibrillation AF is valid atrial fibrillation AF or whether the detection was only due to for example motion artefacts or sporadic premature beats. The clinical professional can optionally combine information on the symptoms of the patient, the heart rhythm abnormalities and the PPG morphology to assess clinical relevance of an atrial fibrillation episode. Thus, the clinical professional can examine the detected atrial fibrillation more efficiently.

It should be noted that although the PPG sensors may be able to provide an AF detection, the output of the PPG sensors may include motion artefacts which may lead to a wrongful atrial fibrillation. Because of the possibility of a wrongful atrial fibrillation detection, for example due to motion artefacts in the output of the PPG sensor, it is advisable that the atrial fibrillation AF detection should be monitored or controlled by a clinical technician, a doctor or a clinical professional. Otherwise the display of atrial fibrillation could lead to false alarms and inappropriately generate anxiety in patients. Thus, the advantages of the non-obtrusive PPG sensors for an unobtrusive and long term monitoring of arrhythmia detection can be combined with the experience of a medical professional.

According to an aspect of the invention, a sensor, such as for example a wearable sensor, is used to detect heart rate data (like heart beat time data) as well as motion data. If an atrial fibrillation is detected, a doctor or a clinical professional can review the raw data of the motion detection and raw output data of the PPG sensor in order to determine whether an actual atrial fibrillation has taken place.

According to the invention, a photo-plethysmographic PPG sensor can be used to detect atrial fibrillation AF unobtrusively and during long periods of time. Because of the nature of the PPG sensor, it is sensitive towards premature beats and motion artefacts. Accordingly, a large amount of suspected AF episodes may be detected which clinical professionals will have to examine in more detail in order to properly evaluate the entity of the AF burden of the patient.

According to an aspect of the invention, the PPG data as well as the motion data and the detected atrial fibrillation AF episodes may be reviewed by a medical professional. Furthermore, symptoms of the patient as well as reference signal templates may be used by the medical professional to examine the suspected AF episodes. By using a (wearable) PPG sensor and by also collecting the corresponding motion data, the effectiveness of the diagnostics of potential atrial fibrillation may be increased. For example, a cardiologist would then be able to verify the detected or suspected atrial fibrillation AF episodes by directly verifying or examining the PPG data as well as the motion data. Additionally, the motion sensor can provide information on the posture and orientation of the body where the PPG signal is collected so that morphology features of the PPG signal could be better evaluated by a human expert. PPG signal templates collected in periods of normal cardiac rhythm for the same orientation of the body location can be displayed together with the PPG signal during AF to facilitate data interpretation. Any meaningful deviation in the PPG morphology for a given body posture/orientation may suggest a true AF episode. Accordingly, the PPG sensor data may be used to detect an atrial fibrillation. The motion data may be used to verify whether the suspected atrial fibrillation episode is related to motion artefacts or not. For example, if the motion sensor has not detected any major movement, the suspected atrial fibrillation episode may be a valid atrial fibrillation episode. However, on the other hand, if the motion detector detects a high amount of motion, the suspected atrial fibrillation episode may not be a valid atrial fibrillation episode but may relate to motion artefacts.

With the system and method according to the invention, it is possible to perform a long term monitoring of the patient's vital signs or cardiac activity such that also a long term atrial fibrillation detection can be performed in an unobtrusive manner.

The PPG sensor data as well as the motion data optionally together with the detected or suspected atrial fibrillation data may be transmitted wirelessly for example via a smart device or directly to an external storage device. Alternatively, the transmission may also be performed when the PPG sensor is connected to a computer or smart device via cable. It shall be understood that a preferred embodiment of the present invention can also be a combination of the dependent claims or above embodiments or aspects with respective independent claims.

These and other aspects of the invention will be apparent from and elucidated with reference to the embodiment(s) described hereinafter.

DETAILED DESCRIPTION OF EMBODIMENTS

Figure 1:
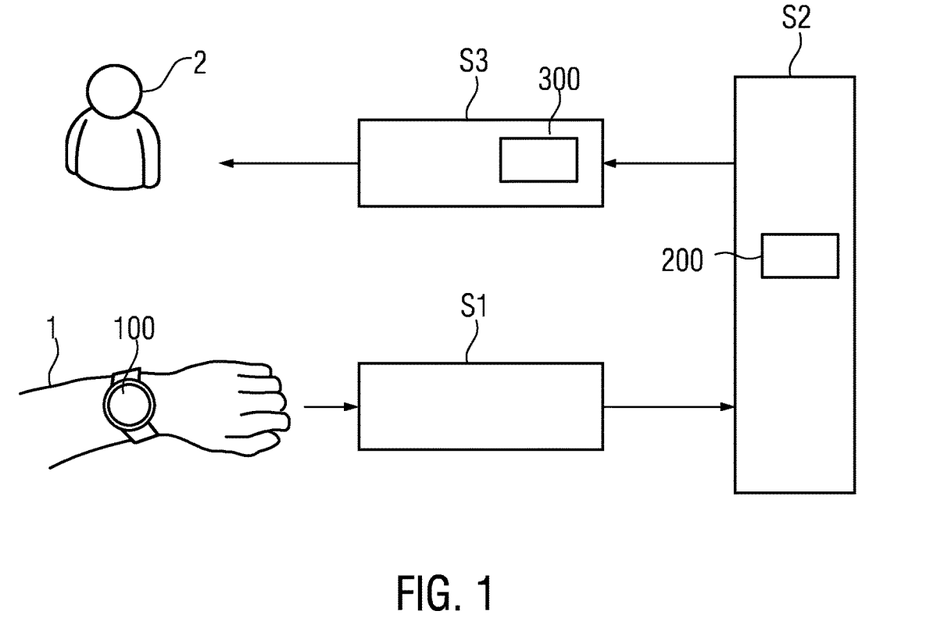
FIG. 1 shows a basic representation of a method of monitoring cardiac activity of a user.

FIG. 1 shows a basic representation of a method of monitoring cardiac activity of a user. A user 1 can wear a vital signs sensor like wearable health monitor 100. The wearable health monitor can be embodied as a wrist worn device and can comprise at least one PPG sensor, a motion detector and optionally a control unit. The wearable health monitor detects heart rate data via the PPG sensor as well as motion, orientation and posture information with the motion detector. The output of the PPG sensor can optionally be analyzed in the control unit in order to detect an atrial fibrillation AF. Alternatively, the analysis of the raw data of the output of the PPG sensor can also be performed in an external device 200.

The PPG sensor outputs an output signal which changes its amplitude with the occurrences of heart beats. The output of the PPG sensor therefore comprises heart rate data. This heart rate data can comprise heart beat time data and/or heart beat rhythm data.

In step S1, the heart rate data (like heart beat time data) as well as the motion data are measured by the wearable health monitor 100. In step S2, the output data of the PPG sensor is analyzed in order to detect possible atrial fibrillations AF. If a suspected or possible atrial fibrillation was detected, the corresponding heart rate data and the motion data are forwarded to an external storage device 200 where the data can be stored and optionally analyzed. The storage and analysis can be performed in step S2. The external unit 200 can be a cloud storage or a smart device or computer to which the wearable health monitor can be coupled to in order to exchange data. Optionally, the heart rate data and the motion data are stored in the health monitor 100 which can be a smart watch or the like.

The stored information can be visualized on a display 300 in step S3 such that for example a doctor or a clinical professional can analyze the output data of the PPG sensor 110 as well as the motion data in order to verify whether an atrial fibrillation AF was detected or not.

In the control unit, optionally an automatic detection of rhythm irregularities can be performed. This can for example be performed using a statistical Markov module. Here, the interbeat interval series is processed. Alternatively, an irregularity of the heart rhythm can be tested using entropy metrics like the sample entropy.

According to an aspect of the invention, heart beat time data can be present in the output signal or output data of the PPG sensor. Based on the heart beat time data, arrhythmia periods are detected. The detected heart rate time data, the detected motion data and the detected arrhythmia periods and in particular the raw signal or raw data of the output of the PPG sensor which were detected during an arrhythmia period can be forwarded to the external device and can be displayed to a medical professional.

Figure 2:
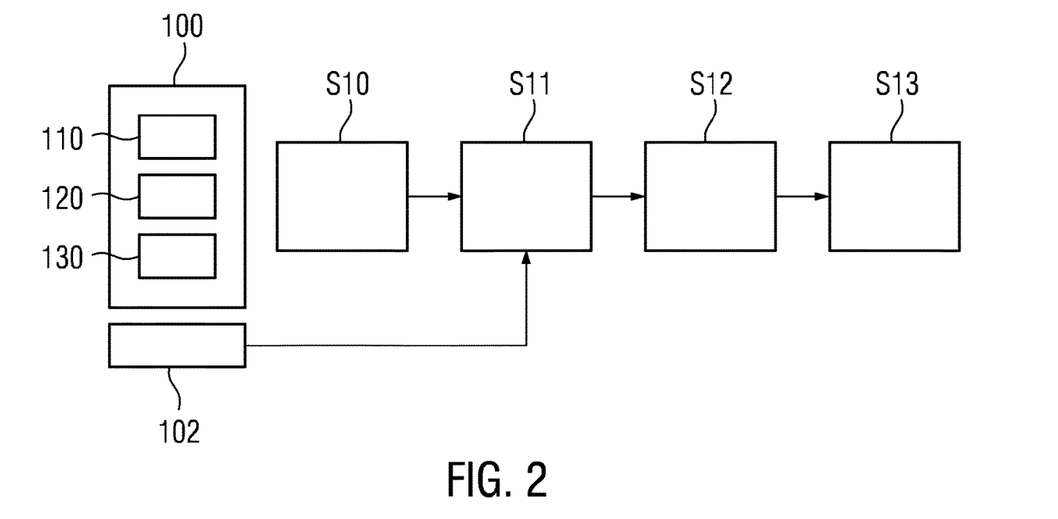
FIG. 2 shows a basic representation of a method of monitoring cardiac activity of a user according to an aspect of the invention.

FIG. 2 shows a basic representation of a method of monitoring cardiac activity of a user according to an aspect of the invention. The wearable health monitor 100 can be embodied as a wrist worn device 100 and can comprise at least one PPG sensor 110, a motion detector 120 and optionally a control unit 130. The wearable health monitor 100 detects heart rate data via the PPG sensor 110 as well as motion, orientation and posture information with the motion detector 120. The output of the PPG sensor 110 can optionally be analyzed in the control unit 130 in order to detect an atrial fibrillation AF. Alternatively, the analysis of the raw data of the output of the PPG sensor 110 can also be performed in an external device 200. It should be noted that in the aspect as described in FIG. 1 or FIG. 2, due to motion artefacts false positive AF classifications can occur in the output signal of the PPG sensor. According to the aspect of FIG. 2, the output of the PPG 110 sensor as well as the output of the motion sensor 120 is analyzed in order to detect an atrial fibrillation AF. In particular, heart beat time data and/or heart rhythm data are analyzed to determine an atrial fibrillation episode. If an atrial fibrillation is detected in step S10, then in step S11 an alert is outputted and optionally the user is asked not to move. Then in step S12, the heart rate of a user can be detected without any motion artefacts, i.e. a motion verification of the expected user action is determined and in step S13, the raw data of the PPG sensor as well as the motion data is detected and can be analyzed.

In other words, if an atrial fibrillation episode AF is detected, the user can be asked to refrain from moving in order to detect the heart rate data again but without any movement to avoid motion artefacts. For example, the user may be asked to keep his arm in a steady position to enable a recollection of the PPG signal to re-evaluate arrhythmias and AF, or the arm or wrist of a user may be positioned in a specific location such as at the chest or the like. Alternatively, the user may be asked to maintain his arms steadily on a flat surface. During this period, the heart rate data as well as the motion data are detected and can be forwarded to the external device.

Optionally, the motion or acceleration data can be used to detect a start and stop of the wrist motion and to detect the orientation of the wrist on which the health monitor is worn.

Accordingly, based on the motion and acceleration data, a wrist position awareness can be achieved. This information regarding the wrist position can be used to generate a reference template and to create advance visualizations of the measured signals like the PPG morphology, heart rate, motion and AF probability.

Accordingly, a position dependent PPG morphology during normal sinus rhythm can be compared to the output of the PPG signal in order to highlight a pathological condition. Optionally, the PPG signal is only collected or the data is only forwarded if the accelerometer has determined a steady position of the wrist. If no steady position of the wrist is detected, then the PPG signal is discarded or the PPG sensor is not activated. Optionally, a measurement record may include the raw PPG data, the acceleration or motion data, the position and orientation of the wrist, the location of the detected pulses due to cardio-vascular activity, an AF probability and symptoms of the user. The symptoms of the user can be inputted to the wearable health monitor.

According to an aspect of the invention, the user may also initiate the above-described measuring procedure if he considers it necessary, for example in case of a sudden unset of cardiac symptoms.

Other types of suspected arrhythmia may also be used as trigger for a user action to perform a motion-controlled acquisition of the PPG signal. For example heart pauses, tachycardia, bradycardia, or other types of supra-ventricular arrhythmias may be automatically detected from the interbeat interval time series and generate alarms for follow up user verification maneuvers.

The data of the PPG sensor and the motion data etc. is stored in a storage device and can be processed later on.

Figure 3:
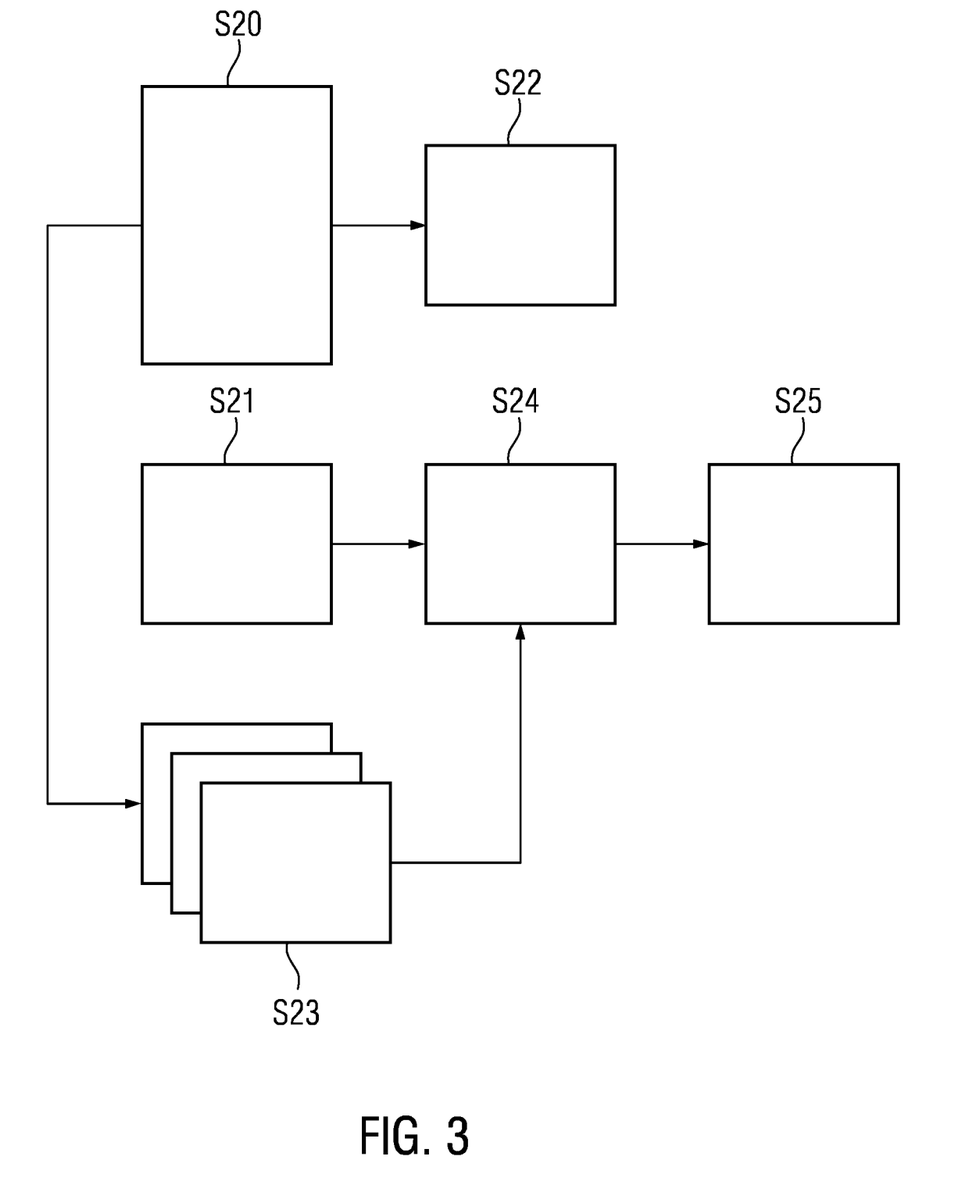
FIG. 3 shows a flow chart of a method of monitoring cardiac activity of a user according to an aspect of the invention.

FIG. 3 shows a flow chart of a method of monitoring cardiac activity of a user according to an aspect of the invention. In step S20, the data of the PPG sensor, motion data, an atrial fibrillation AF probability, symptoms of the user etc. can be detected. In step S21, the motion intensity can be calculated based on the detected motion data. In step S23, position and/or orientation dependent data templates may be generated. In step S22, the PPG signal may be filtered. In step S24, a visualisation engine is used to visualize the PPG data, the motion data as well as optionally a detected atrial fibrillation. In step S25, motion data, detected heart beats, template differences may be highlighted.

Figure 4:
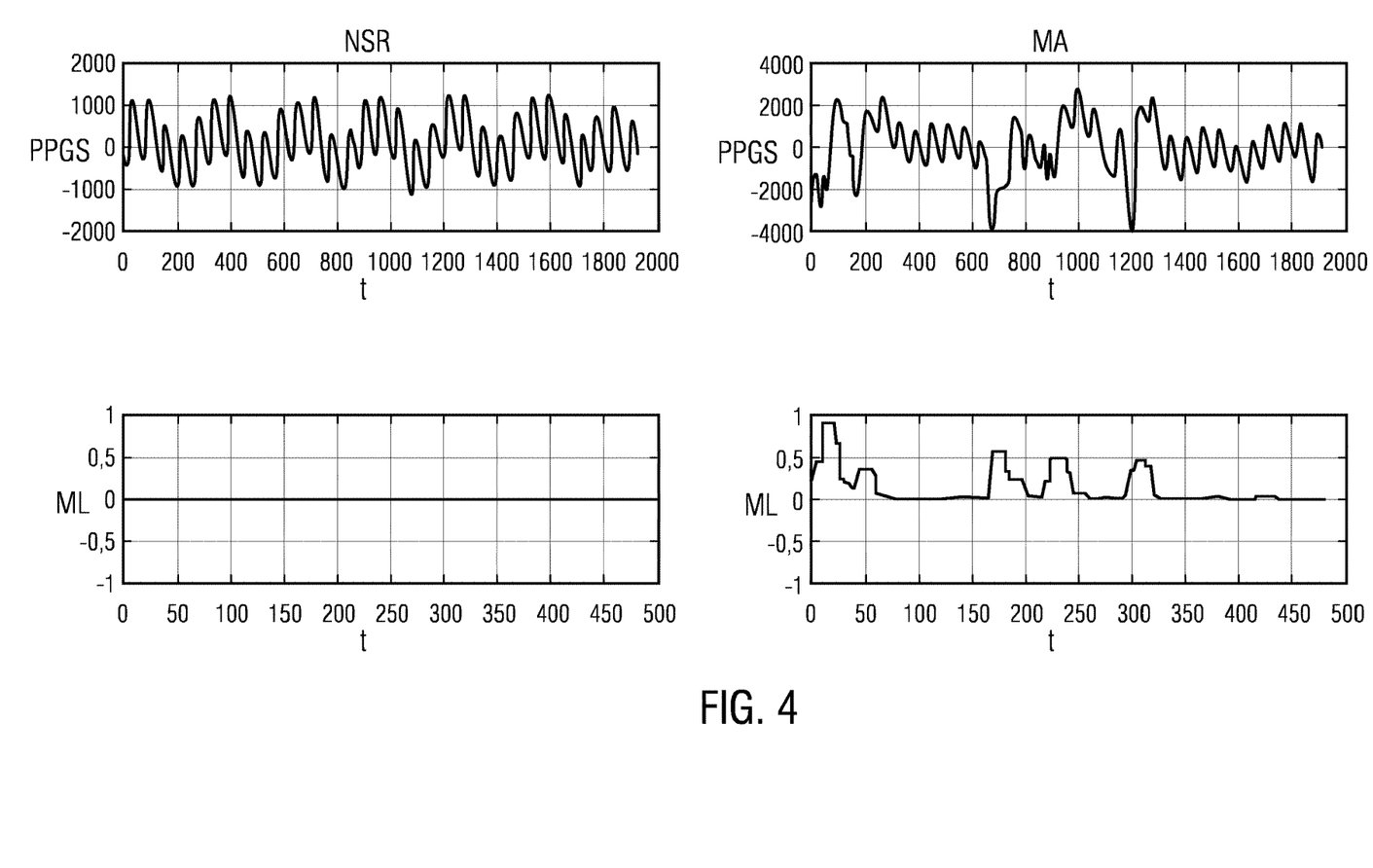
FIG. 4 shows graphs depicting a motion level and an output of a PPG sensor according to an aspect of the invention.

FIG. 4 shows graphs depicting a motion level and an output of a PPG sensor according to an aspect of the invention. In FIG. 4, the PPG signal PPGS and a motion level ML is depicted for a normal sinus rhythm NSR as well as a sinus rhythm without motion artefacts MA as well as with motion artefacts. As can be seen from FIG. 4, a regular peak pattern and the distorted peak pattern is disclosed, wherein the distorted peak pattern is due to motion artefacts.

Figure 5:
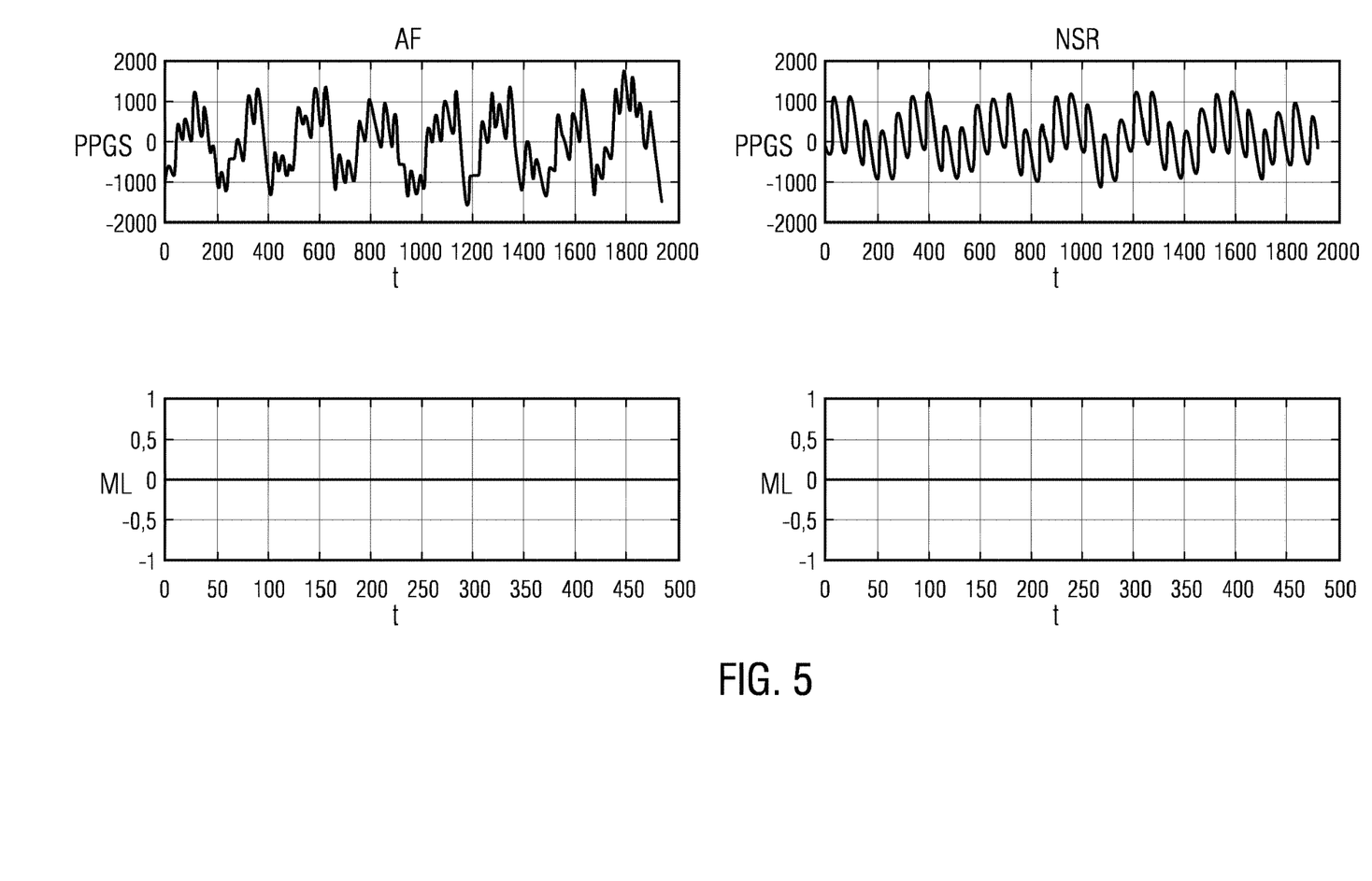
FIG. 5 shows graphs depicting a PPG signal as well as a motion level of a user according to an aspect of the invention.

FIG. 5 shows graphs depicting a PPG signal as well as a motion level of a user according to an aspect of the invention. In FIG. 5, the PPG sensor and motion sensor of a detected atrial fibrillation AF as well as a normal sinus rhythm NSR is depicted. In FIG. 5, a number of irregular peaks with relatively small magnitude is present during an atrial fibrillation AF. As the motion level ML is zero, the output of the PPG sensor PPGS appears to be reliable as no motion artefacts should be present.

Figure 6:
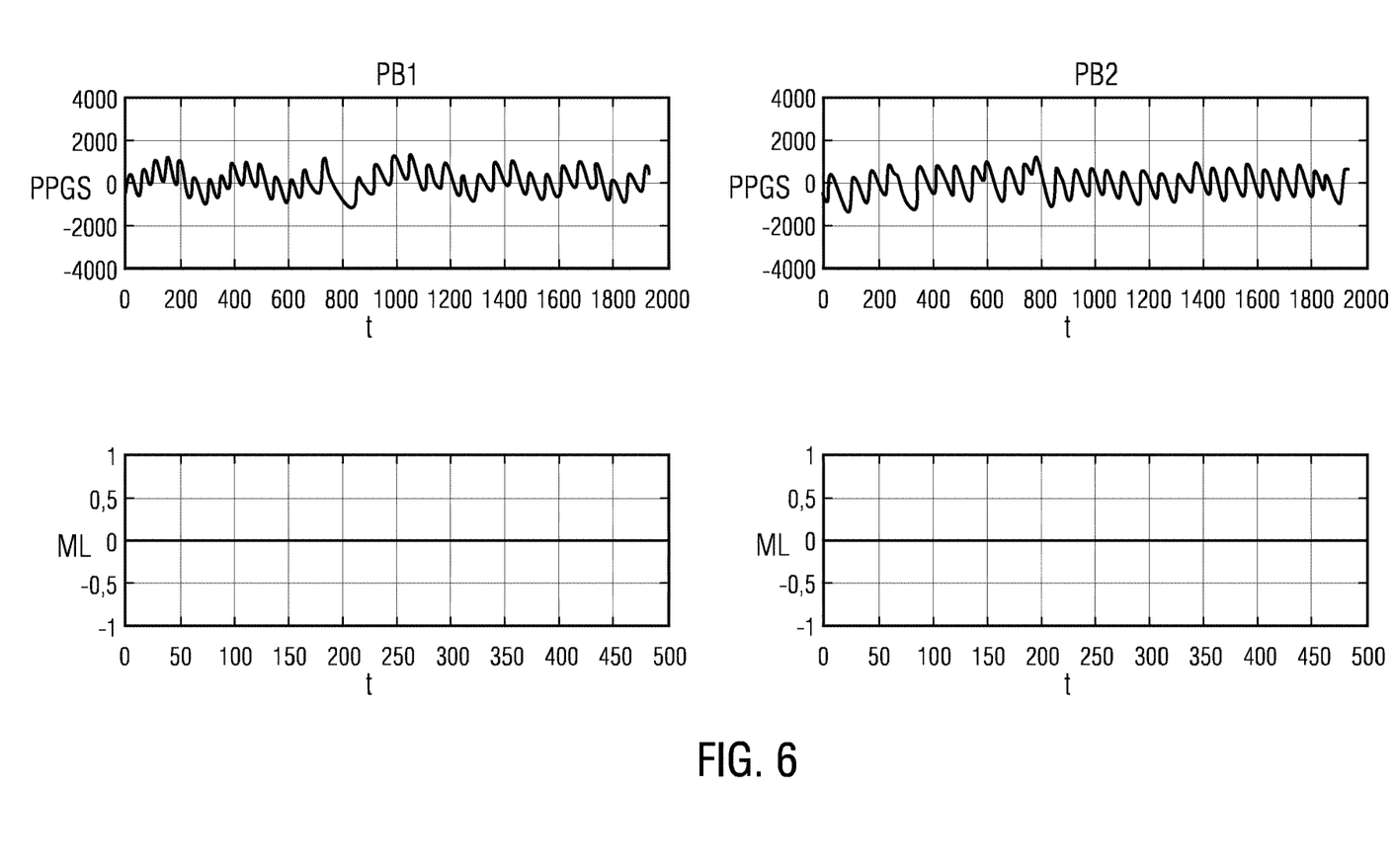
FIG. 6 shows different graphs depicting a PPG signal and a motion level of a user.

FIG. 6 shows different graphs depicting a PPG signal PPGS and a motion level ML of a user. In FIG. 6, the PPG signal as well as the motion level is depicted for a first premature beat PB1 as well as second premature beats PB2. In FIG. 6, the influence of premature beats on the output signal of the PPG sensor is depicted.

According to an aspect of the invention, a position dependent PPG morphology with a normal sinus rhythm as depicted in FIG. 6 can be compared to the actual output of a PPG signal for example as depicted in FIG. 5. By comparing the signals, a pathological condition can be detected.

The PPG signal can optionally be filtered to remove baseline fluctuations for example using a high-pass filter. Accordingly, the output signal may then comprise information such as the temporal location of heart beat and cardiac activity more clearly. The data of the accelerometer or the motion data can be processed to determine a motion level for example by computing the maximum acceleration value on each axis of the accelerometer and allow more straightforward review by a medical professional as to judge whether the filtered PPG signal is affected by motion artefacts as shown in FIG. 4.

The orientation of the wrist or of the body location where the wearable sensor is located during the detection of raw data can be determined by assessing the direction of the gravity component in of a tri-axial accelerometer used as motion sensor in the system. If the wrist is on the chest or on a flat surface, this can be detected. The wrist position and orientation can be used to determine from a data base containing previous recordings from the patient the most relevant PPG template to forward in the visualization tool in order to improve interpretation of the records during clinical review.

In FIG. 5, the raw data of the PPG signal and the motion level are depicted and can be compared to the same data during a normal sinus rhythm. As can be seen in FIG. 5, the actual PPG signal indeed indicates a pathological cardiac activity as the PPG signal morphology shows irregular fluctuations and have a small magnitude as compared to the signals during the normal sinus rhythm.

In FIG. 6, the filtered PPG signal as well as the motion level are depicted for the presence of premature beats. The presence of premature heart beats could lead to a false detection of an AF. However, the medical professional may use the graph of FIG. 6 to determine whether the suspected AF is valid.

The data as depicted in the FIGS. 4 to 6 can be presented to a doctor or a clinical professional such that he can examine the data in order to confirm whether an atrial fibrillation has indeed taken place.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. A method of monitoring cardiac activity of a user, comprising the steps of:
   detecting heart beat time data by a photo-plethysmographic PPG sensor in a health sensor worn by a user;
   detecting motion data by a motion sensor in the health sensor;
   analyzing output data of the PPG sensor comprising heart beat time data to detect suspected arrhythmia periods;
   outputting a message to the user to operate a specific movement protocol with a body part where the health sensor is located to avoid motion artefacts in the output signal of the PPG sensor when the suspected arrhythmia periods are detected;
   detecting heart beat time data and motion data including a health sensor position and orientation during the specific movement protocol;
   analyzing the motion data detected during the specific motion protocol to determine whether the user has followed the specific motion protocol;
   analyzing the heart beat time data detected during the specific movement protocol to detect suspected arrhythmia periods;
   forwarding the detected heart beat time data, the detected motion data and the detected arrhythmia period to an external device, where the data can be stored;
   generating data templates of heart beat time data and heart beat time signal waveforms during the detection of the heart beat time data, said reference templates also include information on health sensor positions and orientations detected during the specific movement protocol;
   displaying the data template of the PPG sensor comprising heart beat time data and a raw signal of the output data of the PPG sensor detected during the suspected arrhythmia periods, the detected motion data as well as at least one previously generated data template to serve as reference such that a medical professional can analyze this data to determine whether the suspected arrhythmia period is a valid arrhythmia period; and
   forwarding the data templates including detected heart beat time data, the detected motion data, the detected arrhythmia period, the health sensor position and orientation to an external device, where the data can be stored for future reference.

2. The method according to claim 1, further comprising the steps of:
   inputting user symptoms;
   detecting heart rate rhythm irregularities in the output data of the PPG sensor; and
   displaying the user symptoms and the heart rate rhythm irregularities together with the output signal of the PPG sensor, the heart rate data, the motion data and the suspected arrhythmia period.

3. The method according to claim 1, wherein the arrhythmia period is an atrial fibrillation period.

4. The method according to claim 1, wherein the arrhythmia period is heart pause period, a tachycardia period, a bradycardia period or supra-ventricular arrhythmia periods.

5. A system of monitoring cardiac activity of a user, comprising:
   a health sensor which comprises a photo-plethysmographic PPG sensor configured to detect heart beat time data, a motion sensor configured to detect motion data of the user and a control unit configured to analyze output data of the PPG sensor comprising heart beat time data to detect suspected arrhythmia periods of the user,
   wherein the health sensor is configured to output a message to the user to operate a specific movement protocol with the body part where the health sensor is located to avoid motion artefacts in the output signal of the PPG sensor when the suspected arrhythmia periods are detected,
   wherein the health sensor is configured to detect heart beat time data and motion data including a health sensor position and orientation during the specific movement protocol,
   wherein the control unit is configured to analyze the motion data to determine whether the user has followed the specific motion protocol and to analyze the heart rate time data detected during the specific motion protocol to determine suspected arrhythmia periods, wherein the health sensor is configured to generate data templates of heart beat time data and heart beat time signal waveforms during the detection of the heart beat time data during the specific movement protocol, wherein said reference template include information on health sensor positions and orientations;

a display unit configured to display the data templates of the PPG sensor, comprising heart beat time data, the detected motion data and the detected raw signal during suspected arrhythmia periods as well as previously generated data templates such that a medical professional can analyze this data to determine whether a suspected arrhythmia period is a valid arrhythmia period; and a storage unit to which the detected heart beat time data, the detected motion data, the detected suspected arrhythmia periods and the data templates are forwarded by the health sensor to be stored for future reference.

6. A non-transitory computer program comprising program code means for causing a system for monitoring cardiac activity of a user to carry out a method of monitoring cardiac activity of a user, when the computer program is run on the system of monitoring cardiac activity of a user the method comprising:

detecting heart beat time data by a photo-plethysmographic PPG sensor in a health sensor worn by a user;

detecting motion data by a motion sensor in the health sensor;

analyzing output data of the PPG sensor comprising heart beat time data to detect suspected arrhythmia periods;

outputting a message to the user to operate a specific movement protocol with a body part where the health sensor is located to avoid motion artefacts in the output signal of the PPG sensor when the suspected arrhythmia periods are detected;

detecting heart beat time data and motion data including a health sensor position and orientation during the specific movement protocol;

analyzing the motion data detected during the specific motion protocol to determine whether the user has followed the specific motion protocol;

analyzing the heart beat time data detected during the specific movement protocol to detect suspected arrhythmia periods;

forwarding the detected heart beat time data, the detected motion data and the detected arrhythmia period to an external device, where the data can be stored;

generating data templates of heart beat time data and heart beat time signal waveforms during the detection of the heart beat time data, said reference templates also include information on health sensor positions and orientations detected during the specific movement protocol;

displaying the data template of the PPG sensor comprising heart beat time data and a raw signal of the output data of the PPG sensor detected during the suspected arrhythmia periods, the detected motion data as well as at least one previously generated data template to serve as reference such that a medical professional can analyze this data to determine whether the suspected arrhythmia period is a valid arrhythmia period; and forwarding the data templates including detected heart beat time data, the detected motion data, the detected arrhythmia period, the health sensor position and orientation to an external device, where the data can be stored for future reference.

7. The method of claim 1, wherein the health sensor is a wearable health sensor to be worn by the user.

8. The system of claim 5, wherein the health sensor is a wearable health sensor to be worn by the user.

\* \* \* \* \*